United States Patent [19]
Jacobsen et al.

[11] Patent Number: 5,939,721
[45] Date of Patent: Aug. 17, 1999

[54] SYSTEMS AND METHODS FOR PROCESSING AND ANALYZING TERAHERTZ WAVEFORMS

[75] Inventors: Rune Hylsberg Jacobsen, Aarhus, Denmark; Daniel Matthew Mittleman, Houston, Tex.; Martin C. Nuss, Fair Haven, N.J.

[73] Assignee: Lucent Technologies Inc., Murray Hill, N.J.

[21] Appl. No.: 08/744,484

[22] Filed: Nov. 6, 1996

[51] Int. Cl.$^6$ ................................ G01N 21/17
[52] U.S. Cl. ............................ 250/330; 250/341.1
[58] Field of Search ................... 250/330, 332, 250/340, 341.1; 382/280; 364/726.02

[56] References Cited

U.S. PATENT DOCUMENTS

| | | | |
|---|---|---|---|
| 5,267,153 | 11/1993 | Shimura et al. | 364/413.13 |
| 5,619,596 | 4/1997 | Iwaki et al. | 382/278 |
| 5,623,145 | 4/1997 | Nuss | 250/330 |
| 5,789,750 | 8/1998 | Nuss | 250/338.1 |

FOREIGN PATENT DOCUMENTS

| | | |
|---|---|---|
| 727671A2 | 8/1996 | European Pat. Off. . |
| 727671A3 | 3/1997 | European Pat. Off. . |

OTHER PUBLICATIONS

Pratt, "Digital Image Processing" John Wiley and Sons, N.Y. (1978) p. 23.

Jacobsen, R.H. et al: "Chemical Recognition of Gases and Gas Mixtures With Terahertz Waves", Optics Letters, vol. 21 No. 24, Dec. 15, 1996, pp. 2011–2013, XP000679220.

Mittleman, D. M., et al: "T–Ray Imaging", IEEE Journal of Selected Topics in Quantum Electronics, vol. 2, No. 3, Sep. 1996, pp. 679–692, XP000689828.

Nuss, M. C., et al: "Chemistry is Right for T–Ray Imaging", IEEE Circuits and Devices Magazine, vol. 12, No. 2, Mar. 1, 1996, pp. 25–30, XP000589127.

Ralph, S. E. et al: "Tetrahertz Spectroscopy of Optically Thick Multilayered Semiconductor Structures". Journal of the Optical Society of America–B, vol. 11, No. 12, Dec. 1, 1994, pp. 2528–2532, XP000570773.

M. C. Nuss, "Chemistry is Right for T–Ray Imaging", *IEEE Circuits & Devices*, Mar. 1996, pp. 25–30.

B. B. Hu et al., "Imaging with terahertz waves" *Optics Letters*, vol. 20, No. 16, Aug. 15, 1995, pp. 1716–1718 (w/Fig. sheet).

M. van Exter, et al., "Carrier dynamics of electrons and holes in moderately doped silicon", *Phys. Rev. B.*, vol. 41, pp. 840–842 (1992).

H. Harde et al., "Thz Commensurate Echoes: Periodic Rephasing of Molecular Transitions in Free–Induction Decay", *Physical Review Letters*, vol. 66, No. 14, 1991, pp. 1834–1837.

M. C. Nuss et al., "Terahertz time–domain measurement of the conductivity and superconducting band gap in niobium", *J. Appl. Phys.*, vol. 70, No. 4, Aug. 15, 1991, pp. 2238–2241.

P. R. Smith et al., "Subpicosecond Photoconducting Dipole Antennas", *IEEE Journal of Quantum Electronics*, vol. 24, No. 2, Feb. 1988, pp. 255–260.

J. T. Kindt et al., "Far–infrared dielectric properties of polar liquids probed by femtosecond terahertz pulse spectroscopy", *J. Phys. Chem.*, vol. 1, p. 10373 (1996).

M. Nuss et al., "Terahertz time–domain spectroscopy", *Millimeter–Wave Spectroscopy of Solids*, ed. George Gruener, Springer–Verlag (Berlin 1997).

*Primary Examiner*—Edward P. Westin
*Assistant Examiner*—Richard Hanig
*Attorney, Agent, or Firm*—J. J. Brosemer

[57] ABSTRACT

A time-domain signal processing system for displaying, classifying, and recognizing temporal and spectral features in terahertz waveforms returned form materials. Specifically, novel techniques are described for classifying and analyzing the free induction decay exhibited by gases excited by far-infrared (terahertz) pulses. Illustratively, a simple geometric picture may be used for the classification of the waveforms measured for unknown gas species and gas mixtures.

13 Claims, 7 Drawing Sheets

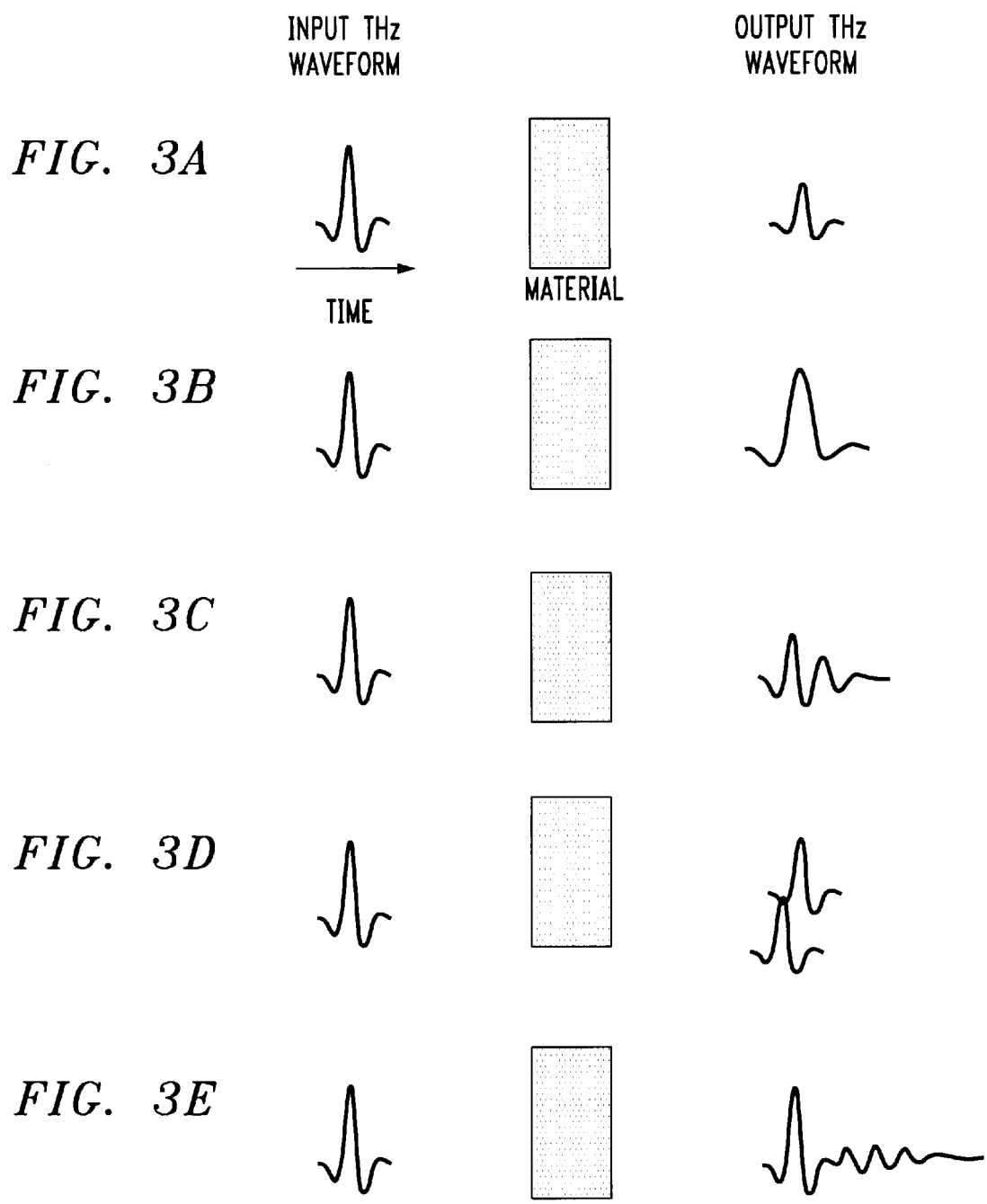

LOW FREQUENCY FILTER
(0.25 – 0.5 THz)

HIGH FREQUENCY FILTER
(1.25 – 1.5 THz)

SYSTEMS AND METHODS FOR PROCESSING AND ANALYZING TERAHERTZ WAVEFORMS

REFERENCE TO RELATED APPLICATIONS

The present invention is related to U.S. patent application Ser. No. 08/388,933, filed on Feb. 15, 1995 and entitled METHOD AND APPARATUS FOR TERAHERTZ IMAGING and U.S. patent application Ser. No. 08/711,146, filed on Sep. 9, 1996, and entitled TERAHERTZ OPTICAL BEAM SYSTEM.

1. Field of the Invention

The present invention relates generally to systems and methods of investigating various media or objects using reflected or transmitted radiation in the terahertz or far-infrared region of the spectrum and, more particularly, to the processing and analysis of terahertz waveforms.

2. Background of the Invention

The terahertz, or far-infrared region of the electromagnetic spectrum has some unique features. For example, THz waves easily penetrate most nonmetallic objects like paper, cardboard, plastics, and moderate thickness of many dielectrics, yet are absorbed by polar materials and liquids. Carriers in semiconductors show strong dielectric response in this region [M. van Exter and D. Grischkowsky, "carrier dynamics of electrons and holes in moderately doped silicon," *Phys. Rev. B.*, vol. 41, pp. 840–842, (1992)], while metals are completely opaque to THz radiation. Polar gases such as water vapor, ammonia, HCl etc. have strong and very characteristic absorption lines in this region of the spectrum [H. Harde, S. Keiding, and D. Grischkowsky, *Phys. Rev. Lett.*, vol. 66, p. 1834 (1991)]. Polar liquids such as water and alcohols also absorb strongly in this frequency range [J. T. Kindt and C. A. Schmuttenmaer, "Far-infrared dielectric properties of polar liquids probed by femtosecond terahertz pulse spectroscopy," *J. Phys. Chem.*, vol. 100, 10373 (1996).] Consequently, the THz spectral range is becoming increasingly important for applications such as remote sensing of gases, quality control of plastic and composite materials, package inspection, and moisture analysis. These features can also be used for imaging in the THz frequency range [B. Hu and M. Nuss, "Imaging with terahertz waves," *Opt. Lett.*, vol. 20, pp. 1716–18, (1995); M. Nuss, "Chemistry is right for T-ray imaging," *IEEE Circuits and Devices*, March 1996]. In addition, the terahertz frequency range has also been of considerable interest in spectroscopy. For example, the electronic properties of semiconductors and metals are greatly influenced by bound states (e.g., excitons and Cooper pairs) whose energies are resonant with THz photons [Nuss et al, "Terahertz time-domain measurement of the conductivity and superconducting bandgap in niobium," *J. Appl. Phys.*, vol. 70, pp. 2238–41, (1991)].

Despite its potential, the use of THz electromagnetic signals for spectroscopy and imaging has been hindered by a lack of suitable tools. For example, swept-frequency synthesizers for millimeter- and submillimeter-waves are limited to below roughly 100 GHz, with higher frequencies being heretofore available only through the use of discrete frequency sources. Fourier transform infrared spectroscopy (FTIR), on the other hand, remains hampered by the lack of brightness of incoherent sources. Additionally, FTIR methods are not useful since the real and imaginary part of response functions must typically be measured at each frequency. Finally, real-time imaging using the THz range of the electromagnetic range has not been possible so far due to the poor sensitivity of detectors in this frequency range.

In U.S. patent application Ser. No. 08/388,933 entitled "Method and Apparatus for Terahertz Imaging" and assigned to the assignee herein, Lucent Technologies, a new spectroscopic imaging technique which overcomes the aforementioned deficiencies was disclosed, which application is expressly incorporated herein by reference in its entirety. This Terahertz ("T-ray") technique is based on electromagnetic transients generated opto-electronically with the help of ultrashort laser pulses (i.e., on the order of several femtoseconds (fs) or shorter). These THz transients are single-cycle bursts of electromagnetic radiation of typically less than 1 picosecond (ps) duration. Their spectral density typically spans the range from below 100 GHz to more than 5 THz. Optically gated detection allows direct measurement of the terahertz electric field with a time resolution of a fraction of a picosecond [Smith et al., *IEEE J. Quantum Electr.*, vol. 24, 255–260, 1988]. From this measurement, both the real and imaginary part of the dielectric function of a medium, which medium may be a solid, liquid, or gaseous composition, may be extracted in a rapid, straight-forward manner [M. Nuss and J. Orenstein, "Terahertz time-domain spectroscopy," in *Millimeter-wave spectroscopy of solids*, ed. George Gruener, Springer-Verlag, (Berlin 1997)]. The brightness of these THz transients exceeds that of conventional thermal sources, and the gated detection is several orders of magnitude more sensitive than bolometric detection.

There is a growing appreciation for the many potential commercial applications in which terahertz spectroscopy and imaging might be exploited [Nuss, "Chemistry is right for T-rays imaging," *IEEE Circuits and Devices*, March 1996, pp. 25–30]. Promising applications include industrial quality and process control, package inspection, moisture analysis, contamination measurements, chemical analysis, wafer characterization, remote sensing, and environmental sensing. A key ingredient to successful exploitation of any of the aforementioned applications, however, is a reliable, computationally practical technique for extracting the relevant spectroscopic information from the THz waveforms for a given application.

As will be readily appreciated by those skilled in the art, when a broad spectrum THz pulse is reflected by or transmitted through a medium under investigation, the acquired waveform contains a large number of data points. Previously, these waveforms have been analyzed by Fourier Analysis, which can be used to extract the frequency dependent absorption coefficient and refractive index of the material under investigation [M. Nuss et al, "Terahertz time-domain measurement of the conductivity and superconducting bandgap in niobium," *J. Appl. Phys.*, vol. 70, pp. 2238–41, (1991); and M. Nuss and J. Orenstein, "Terahertz time-domain spectroscopy," in *Millimeter-wave spectroscopy of solids*, ed. George Gruener, Springer-Verlag, (Berlin 1997)]. Although the frequency dependence of the absorption coefficient and refractive index over the large frequency range encompassed by the THz waveform (e.g., 100 GHz to a few THz) in many cases is unique from material to material, the amount of data which must be compared is too large to be practical for the various applications mentioned above. The inventors herein have thus identified the need for a method by which the relevant spectroscopic information contained in THz waveforms can be compressed to a much smaller set of data points without losing the relevant information contained in the original waveform. Such a compressed data set could be used, for example, to define a pixel in a T-ray image or in the recognition of materials or material compositions.

SUMMARY OF THE INVENTION

For T-ray imaging, the wealth of information contained in the waveforms needs to be compressed so that the relevant information can be extracted, analyzed, and displayed in real time, for example with the help of a digital signal processor (DSP). In the present invention, a number of compression algorithms are devised that allow one to extract relevant information present in the THz waveform returned from a medium, and, optionally, to display the compressed data as pixels of a T-ray image of the medium. Furthermore, compression algorithms are devised that allow one to extract relevant information from the THz waveform returned form different media that are characteristic of the material. Illustratively, each such "classification" of the waveform may be associated with a material, and a code book of compressed waveforms may be compiled against which an unknown waveform can be compared. The objective of such a comparison step is to obtain compositional information about the medium under study.

Depending on the object under investigation, a number of compression techniques are presented in this invention that can be used to accomplish this task. Where only information about the transmissivity or reflectivity of the object is required (i.e., without spectral resolution) such as in package inspection, the compression technique may comprise an integration of the Fourier-transform of the waveform in a certain spectral range to obtain a measure of transmitted or reflected power, or a peak search to obtain the peak signal of the waveform. Because the spot-size for a diffraction-limited focal spot depends inversely on frequency, a partial integration over only the high-frequency portion of the THz frequency spectrum may be sufficient to increase the spatial resolution during T-ray imaging. Conversely, we have discovered that background absorption due to scattering can be largely avoided by integrating only over the low-frequency portion of the spectrum, because scattering increases with the forth power of frequency.

Since THz-TDS is a time-domain technique, another simple yet important compression step is timing extraction. Illustratively, timing extraction may be performed by finding the time-delay of the waveforms after passing through materials. This is useful, for example, in assessing thickness variations, or in determining the position of unknown objects in reflection geometry.

In addition to the simple peak-search method to find the temporal position of a THz waveform after transmission or reflection, the inventors have realized that typical THz waveforms have properties that are similar to mathematical wavefunctions called wavelets. Advantageously, a constant-scale wavelet analysis can be used to determine the temporal position of transmitted or reflected waveforms. Unlike the peak-position method, the wavelet analysis method of the present invention also works in the presence of multiple reflected waveforms, when the temporal position of many, isolated or overlapping THz waveforms has to be found.

In the case of sharp absorption features in the spectrum, such as after passage of THz waves through polar gases, the inventors herein have observed that the action of a resonantly excited gas or gas mixture may be modeled in the time domain by a linear digital filter that reshapes an incident THz waveform to produce a corresponding free-induction decay (FID). According to this aspect of the invention, the free induction decay exhibited by gases excited by far-infrared (terahertz) pulses is analyzed using digital signal processing techniques. These circumstances strongly resemble the basic problems of spectral estimation for phonetic recognition, such that theory and algorithms from speech recognition systems are applicable. Illustratively, a correlation type of analysis known as linear predictive coding (LPC) may be employed to extract and parameterize the spectral features of a waveform. A simple geometric picture enables the use of these parameters for classification of individual gas species as well as quantitative mixture analysis where more than a single gas species is present.

In more general situations, the THz waveforms are modified in both amplitude and phase by transmission through or reflection by the medium under investigation. In this case, more complex signal processing has to be performed to compress the data and extract the relevant information. As noted above, the inventors have observed that the action of a medium can be modeled in the time domain by a linear digital filter that reshapes an incident THz waveform to produce a corresponding output waveform. A very general way of compressing such a linear filter is by use of the digital filter bank method. The inventors have also realized that, in many cases, the mathematical algorithms used for speech processing and recognition can be modified to perform THz waveform processing and recognition.

BRIEF DESCRIPTION OF THE DRAWINGS

The features and benefits of the inventions will be better understood from a consideration of the detailed description which follows taken in conjunction with the accompanying drawings, in which:

FIGS. 3A–3E schematically show how THz waveforms may be altered by transmission or reflection from different materials or objects. From top to bottom: 3A) uniform attenuation, 3B) high-frequency absorption, 3C) frequency-dependent index, 3D) thickness variations, and 3E) sharp absorption lines;

In FIG. 4A, integration over the frequency portion 0.1–0.3 THz of the spectrum is performed; in FIG. 4B, integration over the frequency portion 0.3–0.5 THz of the spectrum is performed; and FIG. 4C depicts integration over the 0.5–0.7 THz frequency portion of the spectrum;

FIGS. 5A and 5B depict T-ray images of strands of human hair, without (right hand side) and with (left hand side) moisturizer applied. The images in FIG. 5A are obtained by integrating the power spectrum over a 0.25–0.5 THz range, while FIG. 5B depicts that use of integration over the 1.25–1.5 THz frequency range;

Figure 9:
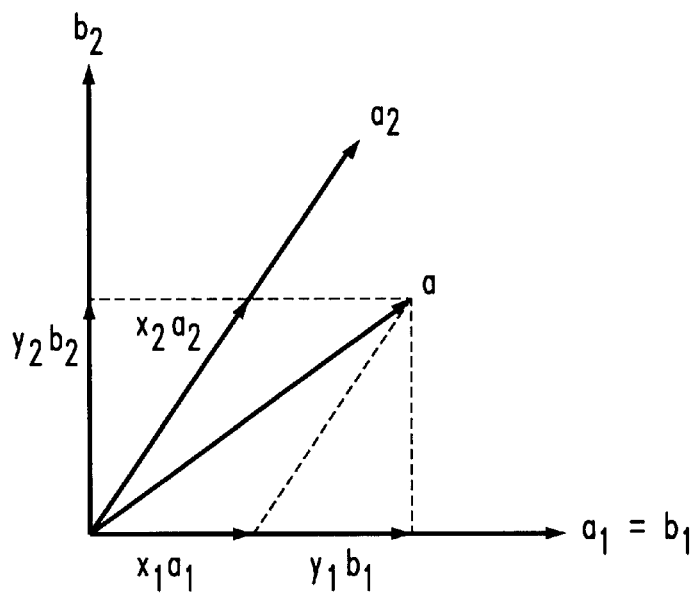
Figure 10:
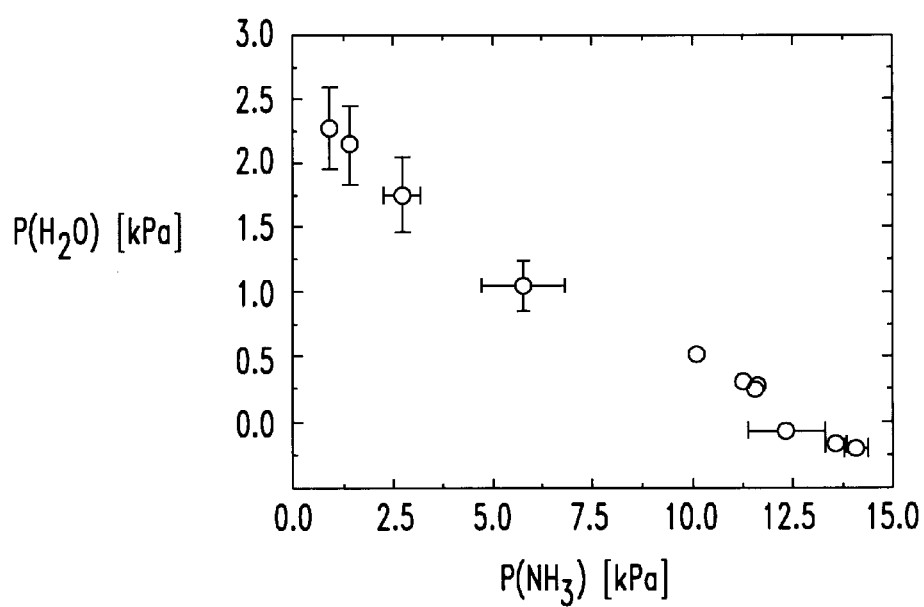

using zero padding techniques to construct an input array of 8192 data points, the thin solid and dotted lines representing the integrated power spectral density for the LPC and Fourier analysis, respectively;

FIG. 9 is a two dimensional LPC vector representation of a binary mixture evaluated in accordance with the technique of the present invention, in which a is the vector sum of the coded vectors for the individual species ($a_i$) weighted by their mole fractions $x_i$, in which $\{b_i\}$ is an orthogonal basis used to calculate the orthogonal projections $y_i$, and in which a linear transformation establishes the relation between the two bases $\{a_i\}$ and $\{b_i\}$; and FIG. 10 is a graphical representation of chemical recognition, in accordance with the present invention, of mixtures of $NH_3$ and $H_2O$, in which each mixture is represented by a single point representing the estimated partial pressure of the two gas species.

DETAILED DESCRIPTION OF THE INVENTION

Figure 1:
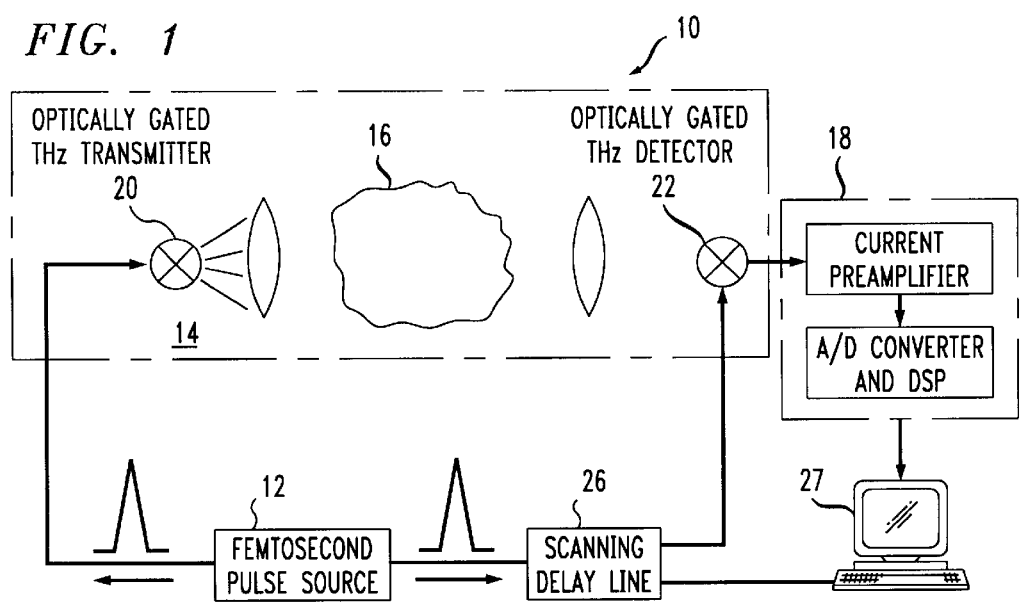
FIG. 1 depicts a THz imaging system employing THz radiation to achieve chemical recognition in accordance with the present invention.

In accordance with the present invention, chemical recognition utilizing THz waveforms is performed using an imaging apparatus such as the one disclosed in U.S. patent application Ser. No. 08/388,933 entitled "Method and Apparatus for Terahertz Imaging". Such an apparatus, indicated generally at 10, is shown in FIG. 1. As can be seen in FIG. 1, THz imaging apparatus 10 includes a source 12 of repetitive optical pulses of femtosecond duration, imaging arrangement 14 by which THz radiation is generated, directed at a medium under investigation 16, and detected upon transmission through or reflection by the medium, and analysis circuitry indicated generally at 18. Source 12 may be configured, for example, as a solid state laser like the Ti:Sapphire laser, which has a wavelength near 800 nm and a typical repetition rate of about 100 MHz. Alternatively, source 12 may be configured as a femtosecond Erbium-Doped Fiber Laser operating at a wavelength near 1.5 $\mu$m. In the illustrative embodiment depicted in FIG. 1, imaging arrangement 14 includes an optically gated THz transmitter 20 and an optically gated THz detector 22. A beam splitter (not shown) divides the output of source 12 into two beams, the pulses of which are used to optically gate transmitter 20 and detector 22. A variable delay line 26, varies the optical delay between the respective gating pulses to acquire a sampled replica of the THz waveform.

Figure 2A:
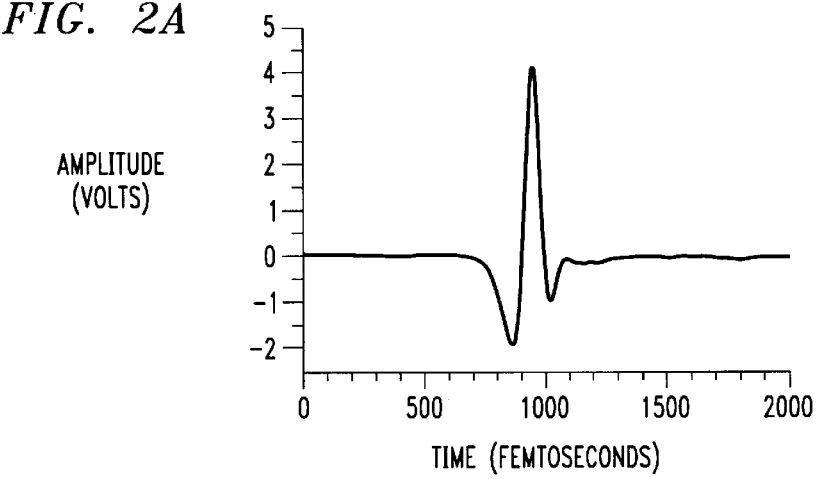
FIG. 2A shows a typical time-domain THz waveform obtained in a system of FIG. 1
Figure 2B:
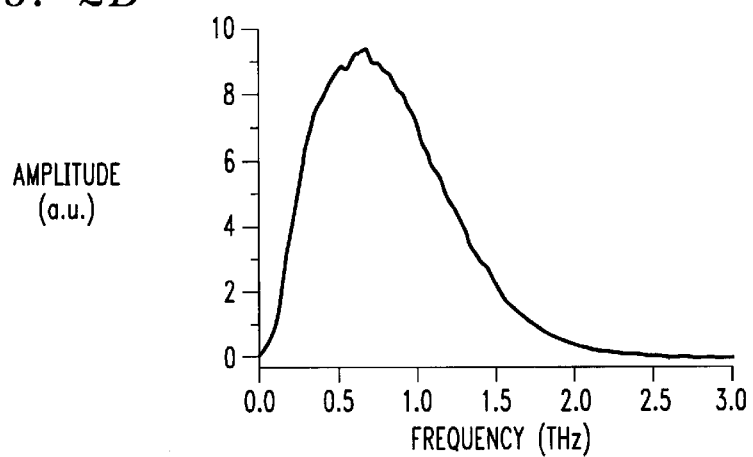
FIG. 2B depicts its power spectrum obtained by a Fourier transform (FFT) of the time-domain waveform.

FIG. 2A shows an exemplary THz waveform obtained by the setup depicted in FIG. 1, and FIG. 2B shows the power spectrum of the THz waveform obtained by computing the magnification of the Fourier transform of the waveform in FIG. 2A.

As discussed in the aforementioned co-pending application, THz imaging apparatus 10 may be employed to analyze temporal distortions of the THz waveforms returned from an object for each pixel in real time to obtain information about the composition or properties of the object at the area illuminated by the THz beam. FIGS. 3A–3E show schematically how THz waveforms may be altered by transmission through an object with different properties. Although this is illustrated by using the example of a transmission geometry, it can easily be appreciated by someone skilled in the art that similar distortions of THz waveforms may occur in reflection. In FIG. 3A, the THz waveform is going through a material with frequency-independent absorption and refractive index, resulting in a returned waveform that is an attenuated replica of the input waveform. As shown in FIG. 3B, high-frequency absorption of the traversed medium leads to selective attenuation of the high-frequency portion of the waveform and consequent broadening of the waveform in the time-domain. In FIG. 3C, the material with frequency-dependent refractive index leads to a "chirped" waveform, in which different frequency components of the waveform travel at different phase velocity, thus leading to a time-dependent frequency variation within the pulse. As shown in FIG. 3D, thickness or index variations of the sample lead to differences in arrival time of the waveform, depending on which portion of the object was traversed by the beam. As shown in FIG. 3E, sharp absorption lines within the spectrum of the THz pulse, such as for polar gases such as water vapor, $CO_2$, HCl vapor, etc., lead to oscillations at the frequencies of the sharp lines in the trailing part of the pulse.

It is known in the field of THz spectroscopy that information about the complex dielectric constant of the material under investigation can be obtained by comparing the frequency-dependent amplitude and phase of the input and returned waveforms. Heretofore, this has been accomplished by computing the complex Fourier transform of both input and returned waveforms, and dividing the complex Fourier spectrum of the returned waveform by the complex Fourier spectrum of the input spectrum. The complex dielectric constant (absorption coefficient and refractive index) can then be obtained by taking a log of the waveform and dividing the result by the thickness of the medium [Nuss, Orenstein, 1997]. Since many materials have characteristic variations in the frequency dependence of their absorption constant and refractive index over the 100 Hz to few THz frequency range covered by the THz waveform, a comparison of the Fourier spectra of the returned THz waveforms can give an indication of and in some cases uniquely identifies the composition of the object.

Figure 4A:
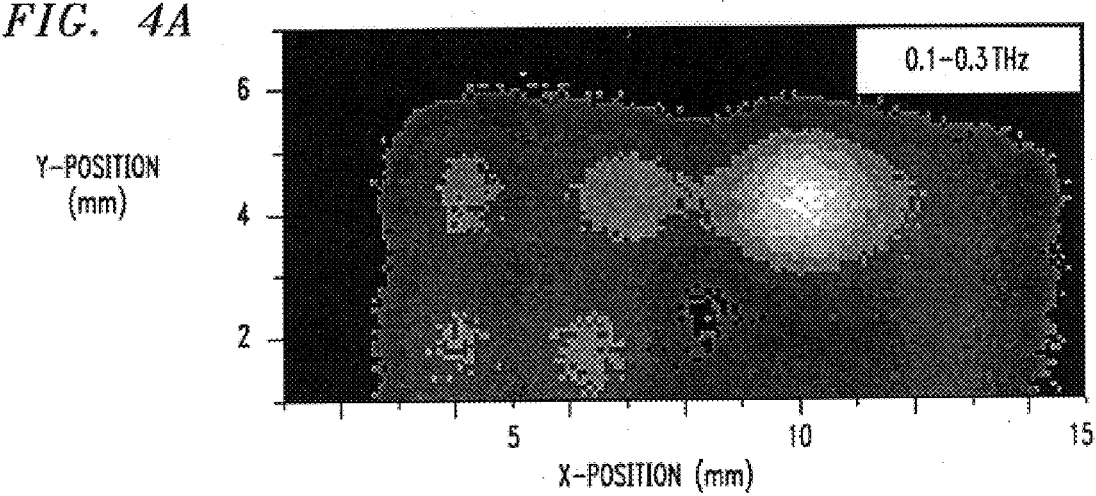
FIGS. 4A–4C show T-ray images of a resolution target. In each case, the digital signal processor performs a FFT of the waveform and integrates over portions of the magnitude of the FFT.
Figure 4B:
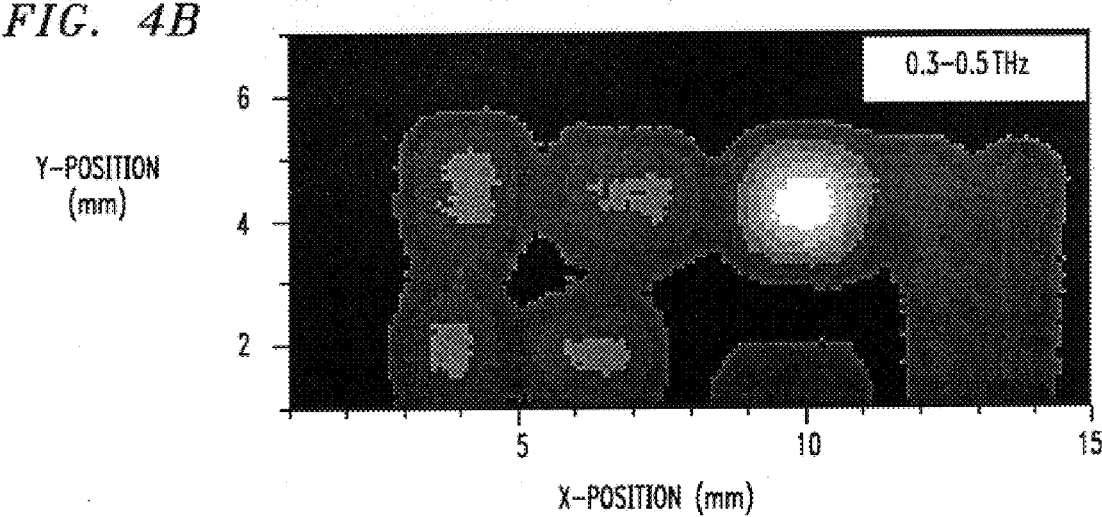
Figure 4C:
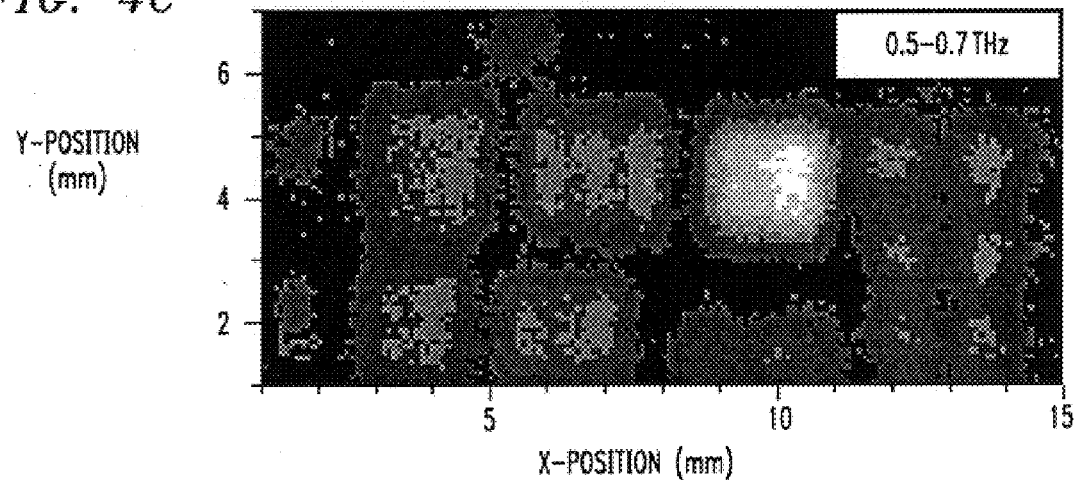

For T-ray imaging, the wealth of information contained in the waveforms needs to be compressed so that the relevant information can be extracted, analyzed, and displayed in real time, for example with the help of a digital signal processor (DSP). Depending on the object under investigation, a number of compression techniques are presented in this invention that can be used to accomplish this task.

Where only information about the transmissivity or reflectivity of the object is required without spectral resolution such as in package inspection, compression can comprise an integration of the Fourier-transform of the waveform in a certain spectral range to obtain a measure of transmitted or reflected power, or a peak search to obtain the peak signal of the waveform. Where the optical system can focus to a diffraction-limited focal spot, as described in U.S. patent application 08/711,146, the spot-size will depend inversely on frequency. Advantageously, only a partial integration—over only the high-frequency portion of the THz frequency spectrum—is needed to increase the spatial resolution during T-ray imaging. As an illustration, illustrative FIGS. 4A and 4C show T-ray images of a resolution target over three frequency ranges wherein the T-ray image has been obtained by integrating the THz spectrum over three different frequency ranges (0.1–0.3, 0.3–0.5, and 0.5–0.7, respectively). In each case, the digital signal processor performs a FFT of the waveform and integrates over portions of the magnitude of the FFT. Because the of the capability of the system to focus to a diffraction limited spot, i.e., with a spot size that varies inversely proportional to the frequency, integration over the high-frequency portion of the power spectrum leads to images with better spatial resolution.

Figure 5A:
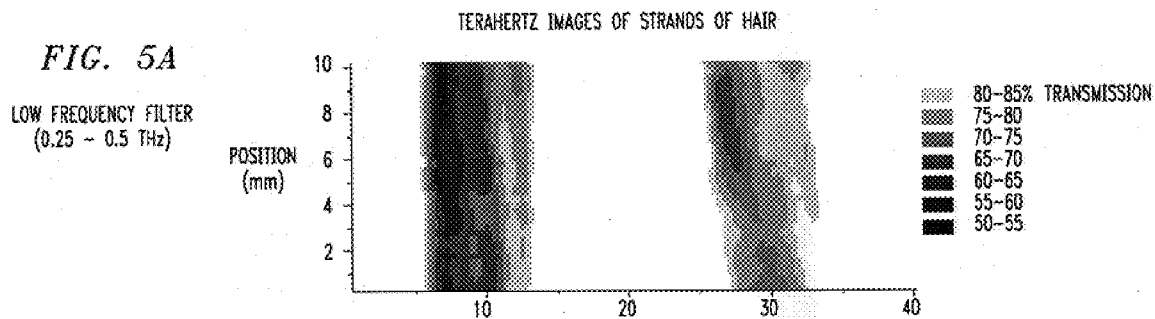
Figure 5B:
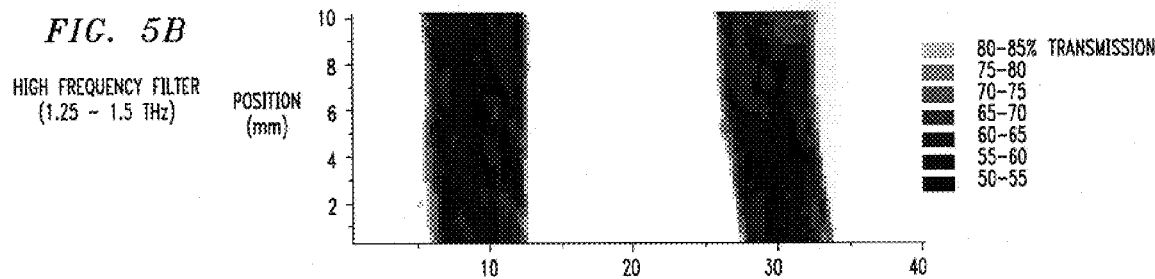

We have further discovered that background absorption due to scattering can be largely avoided by integrating only over the low-frequency portion of the spectrum, because scattering increases with the forth power of frequency. Scattering can be particularly severe when the size of the scattering centers approaches the wavelength of the THz radiation, which is about 300 mm for a 1 THz center frequency. FIGS. 5A and 5B depict T-ray images of strands of human hair, untreated, and with treated moisturizer applied. The images in FIG. 5A are obtained by integrating the power spectrum over a 0.25–0.5 THz range, while those in FIG. 5B depict results obtained by integrating over the 1.25–1.5 THz frequency range. In the T-ray images obtained using high-frequency components of the spectrum, it is difficult to see the added absorption due to the additional moisture on the left hand side because of the strong background absorption due to scattering. On the other hand, a T-ray image obtained by integrating over only the low-frequency components of the power spectrum clearly shows the difference due to the presence of moisture in the hair.

Figure 6:
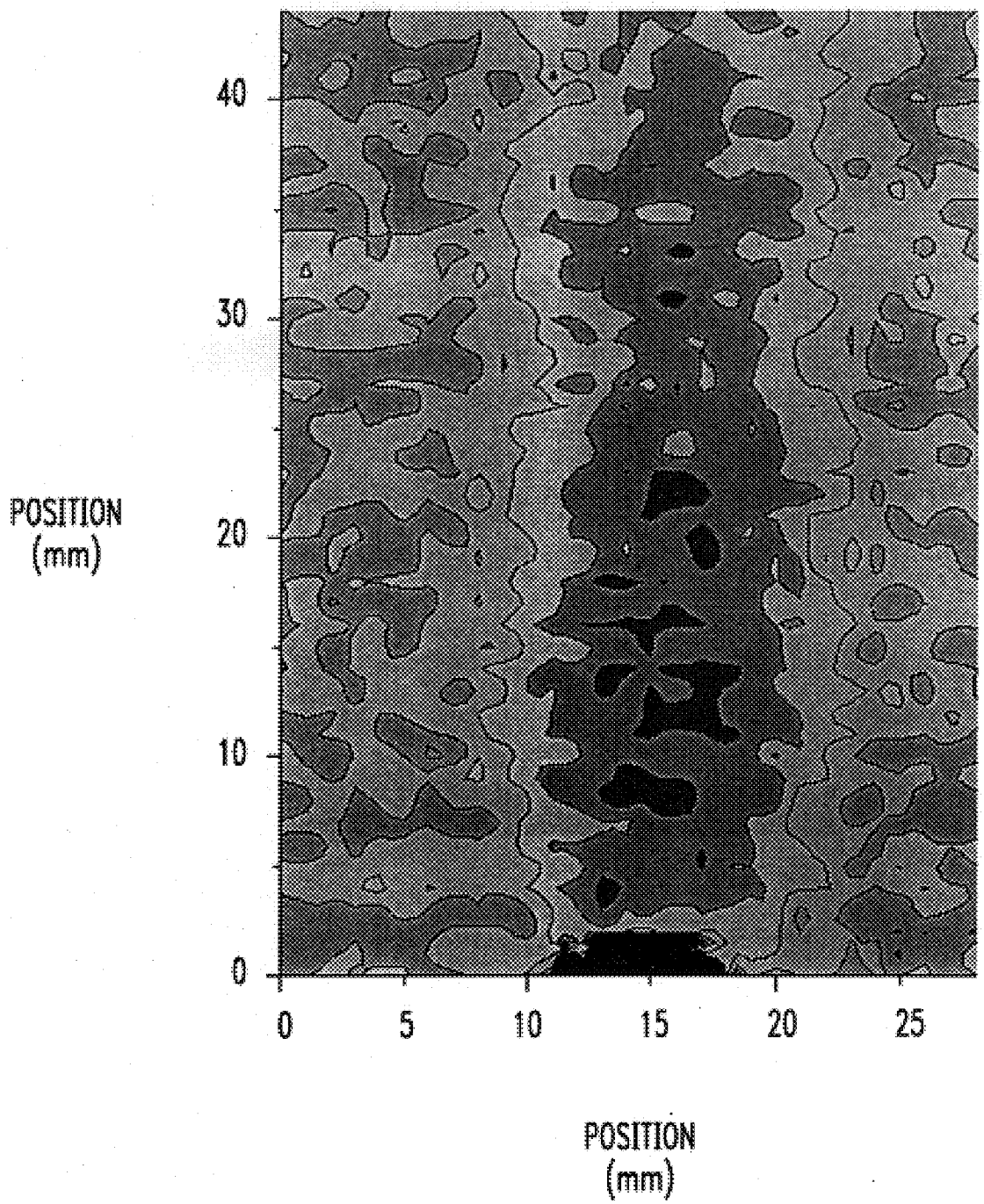
FIG. 6 shows a T-ray image of a flame, obtained by measuring the difference in arrival time of the focused THz pulses through the flame.

Because THz-TDS is a time-domain technique, another simple yet important compression step is timing extraction, for example by finding the time-delay of the waveforms after passing through materials. This is useful for example in assessing thickness variations, or in determining the position of unknown objects in reflection geometry. As an example, FIG. 6 shows a gray scale T-ray image of a flame, obtained by measuring the difference in arrival time of the focused THz beams through the flame. The DSP was instructed in this case to determine the peak position of the waveform in time and apply a gray scale to the temporal shift of the waveform. Each contour corresponds to a 5 femtosecond incremental shift in time delay. It will be appreciated from FIG. 6 that, although the duration of the THz pulse is on the order of 1 ps, the position of the peak of the waveform can be determined with an accuracy approaching a few femtoseconds.

In addition to the simple peak-search method to find the temporal position of a THz waveform after transmission or reflection, the inventors have observed that typical THz waveforms have properties that are similar to mathematical wavefunctions called wavelets [M. Vetterli and J. Kovacevic, "Wavelets and Subband Coding," Prentice-Hall, (1995) reference]. Therefore, the inventors have recognized that a constant-scale wavelet analysis can conveniently be used to determine the temporal position of transmitted or reflected waveforms. Unlike the peak-position method, the wavelet analysis method also works in the presence of multiple reflected waveforms, when the temporal position of many, isolated or overlapping THz waveforms has to be found.

In the case of sharp absorption features in the spectrum, such as after passage of THz waves through polar gases, the inventors have identified that the action of a resonantly excited gas or gas mixture can be modeled in the time domain by a linear digital filter that reshapes an incident THz waveform to produce a corresponding free-induction decay (FID). Extraction and analysis of the spectral features of the modeled waveform may be performed using techniques similar to those employed for phonetic recognition. By way of illustrative example, a correlation type of analysis known as linear predictive coding (LPC) may be used to extract and parameterize the spectral features of a waveform. Linear prediction is an efficient model for analyzing sharp spectral features. The waveform is treated as a result of an all-pole filtering of a noise input and the filter coefficients are the parameters of the LPC. Ideally, all the spectral information is transferred to the filter coefficients and the input becomes white noise.

In accordance with the present invention, the measured waveform is expressed as a linear combination (i.e. a weighted sum) of its past M values. The waveform is denoted s(n), and is measured at points equally spaced in time. By including an error term, e(n), the sampled waveform can be expressed:

$$s(n) = \sum_{k=1}^{M} a_k s(n-k) + e(n), \qquad 1$$

where e(n) is the residual that accounts for the equality to hold, and $a_k$ are the parameters of the linear prediction. As will be readily appreciated by those skilled in the art, an LPC model can be described in both the time, t, and the frequency domain f. In the interest of clarity and simplicity of illustration, only a frequency formulation will be described in detail herein. It should, however, be emphasized that the experimental implementation presented below is based directly on a time-domain analysis and does not involve Fourier-transformations To illustrate the basic physical concepts involved, the z-transform of Eq. (1) is presented:

$$S(z) = \sum_{k=1}^{M} a_k z^{-k} S(z) + E(z), \qquad 2$$

where z=exp(i2πfΔ) and Δ−1 is the sampling frequency. One finds that the signal, S(z), is constructed from the residual, E(z), by an all-pole filtering:

$$S(z)=H(z)E(z), \qquad 3$$

where $$H(z) = \frac{1}{1 - \sum_{k=1}^{M} a_k z^{-k}}. \qquad 4$$

The LPC coefficients, $a_k$, contain the "information" of the spectral content of the waveform. The advantages of using LPC for chemical recognition of gases are threefold. First, poles provide an accurate representation for an underlying power spectrum that has sharp spectral lines. This is in contrast to Fourier analysis where a signal waveform is expanded into a Fourier series. Such series can have only zeros, not poles, and must attempt to fit sharp spectral features with a polynomial which requires a large number of coefficients. Second, by using LPC one can always rely on the same number of coefficients, M, regardless of the number of resonances excited. Accordingly, simple geometric pictures can be used instead of complicated template matching techniques for the classification of waveforms. Finally, the algorithms for LPC analysis may be executed quickly and the implementation is suitable for parallel processing in contrast to Fourier analysis where the entire waveform has to be sampled before further processing.

The optimum values for the LPC coefficients are calculated from least square principles, that is, it is desired to minimize the total squared residual: $\epsilon=\Sigma e(n)^2$. The analysis yields a system of normal equations that relates the LPC coefficients to values of the autocorrelation function, $\Sigma k\ s(k)s(k-n)$, of the time series representing the waveform. The problem can be solved in terms of numerical matrix inversion schemes such as the Levinson-Durbin algorithm or by using Burg's algorithm for maximum entropy spectral analysis. For a detailed discussion of these algorithms and of their application, reference may be had to a book entitled *Digital Signal Processing, Principles, Algorithms, and Applications*, by. J. G. Proakis and D. G. Manolakis, Prentice Hall, N.J. (1993).

In the previous examples, compression algorithms for THz waveforms have been presented that extract certain relevant information from the waveform. The compressed data set can now either be displayed to produce a T-ray image, or can be further processed for the purpose of extracting compositional information about the medium under investigation. In the context of the present invention, the compressed data set is treated as a vector in a high dimensional vector space. If the vector represents a known species, it can be stored in a code book for later use in a recognition procedure—with each material of interest corresponding to one vector in the code book. Accordingly, when it is desired to recognize an unknown species, one may measure the THz waveform, extract the vector parameters, and perform a comparison with the known species from the code book. In the following, this procedure is illustrated using the example of gas recognition and Linear Predictive Coding (LPC) as compression and classification procedure:

In accordance with an illustrative embodiment of the present invention, the parameters from an LPC analysis are treated as a vector, $a=(a_1, a_2, \ldots a_M)$, in an M-dimensional vector space. Vectors representing known gas species are stored in a codebook, and by successive measurements and subsequent LPC analysis for a variety of different gases, the codebook is built. The final codebook contains a set of linearly independent vectors $\{a_i\}, i=1,2,\ldots,p$ and $p<M$, that span a subspace of the M-dimensional vector space. A single-species-recognition procedure consists in a full search through the codebook to find the "best" match between the trial vector, i.e., the LPC coefficients of an unknown species, and the vectors in the codebook. This is accomplished, for example, by calculating the Euclidean distances between the trial vector and the coded vectors and use the minimum distance as classification criteria.

Gas mixture analysis according to the present invention is made possible by the fact that the LPC vectors from different gases add in the M-dimensional vector space. Hence, a coordinate representation, $x_i$, of the trial vector in the $\{a_i\}$-basis becomes a measure of the mole fractions of the species present in the mixture. These principles are illustrated in FIG. 9 using a binary mixture as an example. The LPC vector representing the mixture, a, is the vector sum of the coded vectors for the individual species ($a_1$ and $a_2$) weighted by their mole fractions. In practice, an orthogonal basis, $\{b_i\}$, is constructed and is used to calculate the orthogonal projections $y_i$. A linear transformation establishes the relation between the two bases $\{a_i\}$ and $\{b_i\}$.

Chemical recognition in accordance with the present invention was evaluated experimentally by using the arrangement 10 of FIG. 1 to obtain sampled replicas of THz waveforms. Four gases, HCl, $NH_3$, $H_2O$ and $CH_3CN$, in a pressure range of from 0.3 to 13 kPa, were evaluated by placing them into a gas cell 30.5 cm in length. In each experiment, a collimated THz beam was transmitted through the gas cell.

Figure 7:
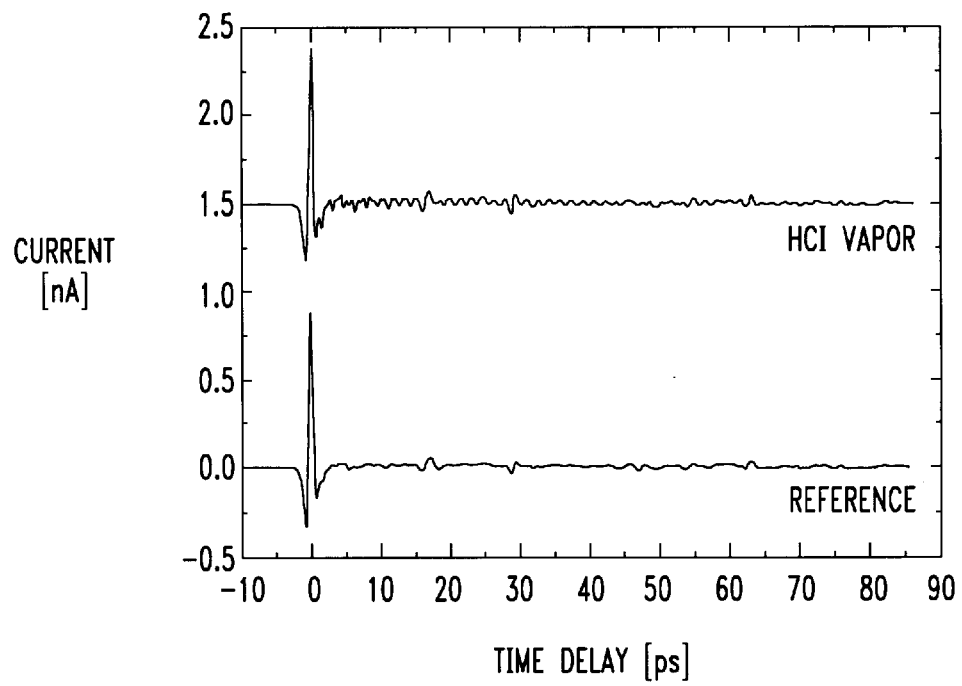
FIG. 7 is a THz waveform for HCl vapor at 13 kPa and a reference waveform measured for an evacuated gas cell, the HCl waveform being shifted by 1.5 nA for clarity.

With particular reference to FIG. 7, there is shown an example of a THz waveform resulting from propagation in an HCl atmosphere at a pressure of 13 kPa. The measured FID shows fast oscillations due to the frequency beating between resonances at 0.626, 1.251 and 1.876 THz. [H. M. Pickett, R. L. Poynter, and E. A. Cohen, *Submillimeter,* *Millimeter*, and *Microwave Spectral Line Catalog*, accessed via World Wide Web (http://spec.jpl.nasa.gov) from the Jet Propulsion Laboratory, Pasadena Calif.]. Also shown in FIG. 7 is a reference waveform measured using an evacuated gas cell. The waveforms were obtained by sampling N=1024 points with a temporal resolution of $\Delta=93$ fs.

Prior to the LPC analysis, the measured waveforms were preprocessed using finite impulse response filtering and time-domain windowing. That is, the sampled waveform was convoluted with the impulse response of a bandpass filter and is multiplied by window functions. This is performed to stabilize the LPC by reducing the risk of predicting spurious frequency peaks and eliminating frequencies beyond the bandwidth of the THz pulse. Because only the coherent irradiance from the gas is of interest (not the spectrum of the source), LPC analysis commences with values appearing after the impulse excitation.

Figure 8:
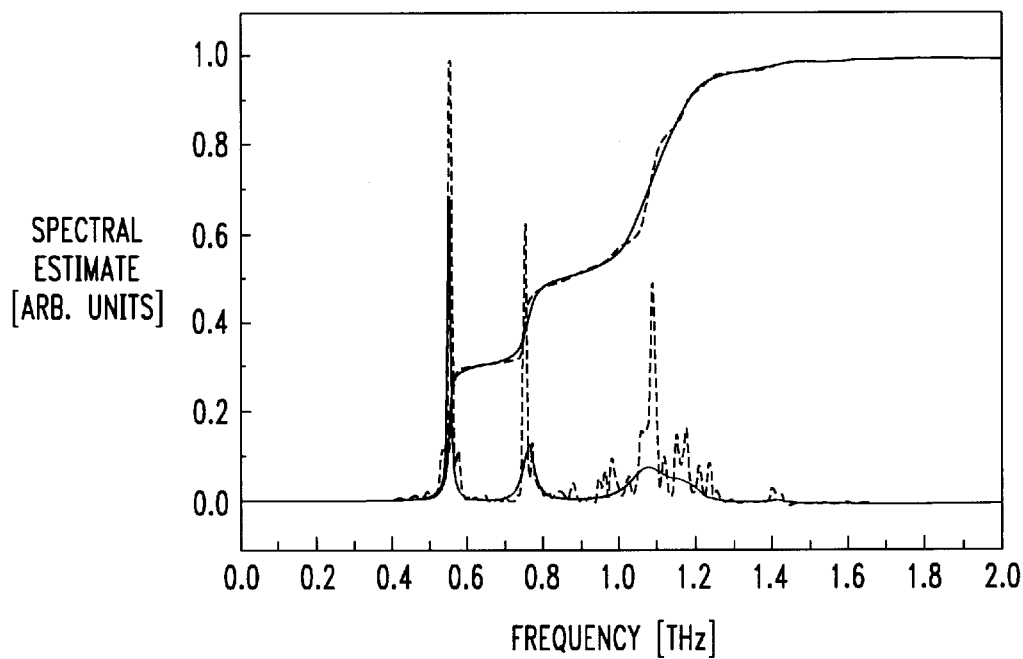
FIG. 8 is a power spectrum estimate, using $H_2O$ at a pressure of 2.8 kPa, from an LPC analysis of order M=50 (thick solid line) and from a Fourier analysis (dashed line)

The LPC coefficients obtained in the manner described above can be used for a power spectrum estimation of the input waveform. This technique is known as the maximum entropy method (MEM) and is described in the text by Rabiner and Juang referenced above. FIG. 8 shows a comparison between the maximum-entropy-method (MEM) power spectrum, calculated from the LPC coefficients (solid line) and the Fourier-transform power spectrum (dashed line) for a waveform that has been propagated through $H_2O$ vapor at 2.8 kPa. The MEM spectrum is estimated from the power spectrum of the all-pole filter, $$|S(z)|^2 \approx a_o |H(z)|^2,$$

where $a_o=\min(\epsilon)$ is the minimum squared residual. The comparison between the two spectra, while not used for recognition purposes, is useful as a confidence measure of the LPC. The frequency resolution obtained from the Fourier analysis is better that the resolution obtained from the LPC. However, the LPC analysis correctly predicts the power, i.e., the integral of the power spectral density, in an absorption line. For comparison, the inset on the figure shows the magnitude of the Fourier-transform of our source.

A gas mixture determination in accordance with the present invention relies on the fact that the LPC vectors corresponding to different gases add. Hence, a coordinate representation, $x_i$, of the trial vector in the $\{a_i\}$-basis becomes a measure of the mole fractions of the species present in the mixture. j These principles are illustrated in FIG. 9 using a binary mixture as an example. The LPC vector representing the mixture, a, is a vector sum of the coded vectors for the individual specias ($a_1$ and $a_2$) weighted by their mole fractions. In practice, an othrogonal basis, $\{b_i\}$, is constructed and is used to calculate the orthogonal projections $y_i$. A linear transformation establishes the relation between the two bases $\{a_i\}$ and $\{b_i\}$. From the projections of the resulting vector onto the vectors in the codebook, one can determine the mole fractions of the various species. To demonstrate the use of the chemical recognition system for mixture analysis a binary mixture of $NH_3$ and $H_2O$ was evaluated. The result is shown in FIG. 10.

The mixtures were prepared starting with $NH_3$ vapor at 12.9 kPa and successively exchanging with $H_2O$ vapor in increments of a few percent per volume. For each mixture, a THz waveform was recorded. From the LPC analysis and the geometric interpretation of the LPC vector, mole fractions of the two species were calculated. The mole fractions are converted into partial pressures by scaling to the pressure of the corresponding coded vectors. Nonvanishing projections onto species in the codebook, which were not present in the mixture (HCl and $CH_3CN$), are attributable to experimental uncertainties and are used to estimate error bars. Error bars are only displayed when they become larger than the actual data point.

From FIG. 10, we find that the chemical recognition system is capable to trace the transition from $NH_3$-dominated mixtures (lower right) to the $H_2O$-dominated mixtures (upper left). When a mixture is strongly dominated by $NH_3$ the prediction yields a slightly negative pressure for $H_2O$ and a pressure for $NH_3$ that is larger than the starting pressure. Obviously, this situation does not have any physical meaning, and results from insufficient statistics for the coded vectors. By using clustering techniques of vectors obtained from repeated measurements on a particular gas species we should be able to account for this inaccuracy. One clustering techniques which is suitable for this purpose is disclosed in a text by L. Rabiner and B. -H. Juang entitled *Fundamentals of Speech Recognition* (Prentice Hall, 1993).

The algorithms used in accordance with the illustrative embodiment of the present invention discussed in detail above have been chosen to be suitable for real time application. The recent progress in digital signal processing (DSP) technologies allows such an approach to be implemented in an easy and inexpensive manner. It should, however, be readily appreciated by those skilled in the art that although a DSP implementation is preferred, discrete filters may also be employed to obtain the filtering coefficients used in the illustrative embodiment described above using LPC and, in fact, that alternate classification algorithms may be utilized instead of LPC. It will therefore be recognized that the embodiments shown and described in detail herein are intended to be merely illustrative of the inventive concepts involved. Various other embodiments and modifications may be made by those skilled in the art without departing from the spirit and scope of the invention.

What is claimed is:

1. A method of processing and analyzing Terahertz waveforms returned by a medium having at least one constituent, comprising the steps of:

receiving terahertz waveforms that are one of transmitted through or reflected by the medium;

obtaining digitally sampled replicas of the received terahertz waveforms; compressing the digitally sampled replicas into respective data sets of reduced size;

displaying said reduced size data sets as pixels of an image of the medium, each pixel being representative of the terahertz waveform returned from a distinct portion of the medium illuminated by an incident terahertz pulse.

2. The method of claim 1, wherein said compressing step includes:

integrating portions of a power spectrum obtained from a FFT of the returned waveform to thereby obtain a measurement of received power proportional to the power within said portions of the spectrum.

3. The method of claim 2, wherein said step of integrating comprises integrating higher frequency portions of the obtained power spectrum to thereby obtain enhanced spatial resolution.

4. The method of claim 2, wherein said step of integrating comprises integrating lower frequency portions of the obtained power spectrum to thereby remove scattering background.

5. The method of claim 1, wherein said step of compressing includes determining a peak amplitude of the returned waveform to thereby obtain an approximation of the received power.

6. The method of claim 1, wherein said step of compressing includes determining whether or not an amplitude of the returned waveform exceeds a particular threshold to thereby determine the presence or absence of an object.

7. The method of claim 1, further including a step of measuring arrival time of the returned waveform to thereby ascertain a temporal delay of the terahertz waveform following transmission through or reflection by the medium.

8. The method of claim 7, further including, when a refractive index of the medium is substantially constant, a step of using temporal delay information to identify variations in the thickness of an object at multiple, spatially distinct locations traversed by terahertz waveforms.

9. The method of claim 7, further including, when thickness of the medium is substantially constant, a step of using temporal delay information to identify variations in the refractive index of an object at multiple, spatially distinct locations traversed by terahertz waveforms.

10. The method of claim 2, further including, when thickness of the medium is substantially constant, a step of using the measurement of received power to identify variations in absorption coefficient of the medium at multiple, spatially distinct locations traversed by terahertz waveforms.

11. The method of claim 2, further including a step of using the measurement of received power to identify variations in reflection coefficient of the medium at multiple, spatially distinct locations.

12. The method of claim 7, wherein the arrival time is measured by locating a peak value of the waveform.

13. The method of claim 7, wherein the arrival time is determined by performing a wavelet analysis on the returned waveform.

* * * * *